United States Patent [19]

Alterman et al.

[11] Patent Number: 4,859,234
[45] Date of Patent: Aug. 22, 1989

[54] HERBICIDAL COMPOSITIONS OF ACYLATED 1,3-DICARBONYL HERBICIDES AND PHENOXYALKANOIC ACIDS, SALTS, AMIDES AND ESTERS THEROF AS ANTIDOTES

[75] Inventors: Marcelo K. Alterman, Wilton, Conn.; Luis F. do Amaral, Campinas, Brazil

[73] Assignee: ICI Americas Inc., Wilmington, Del.

[21] Appl. No.: 95,788

[22] Filed: Sep. 14, 1987

[51] Int. Cl.$^4$ .............................................. A01N 41/10
[52] U.S. Cl. ......................................... 71/103; 71/88; 71/90; 71/91; 71/92; 71/94; 71/98; 71/105; 71/108; 71/109; 71/110; 71/116; 71/117; 71/123
[58] Field of Search .................................. 71/103, 117

[56] References Cited

U.S. PATENT DOCUMENTS

| | | | |
|---|---|---|---|
| 2,577,969 | 12/1951 | Jones | 71/117 |
| 3,131,509 | 5/1964 | Hoffman | 71/103 |
| 4,001,006 | 1/1977 | Nash | 71/117 |
| 4,416,687 | 11/1983 | D'Amrco et al. | 71/118 |

FOREIGN PATENT DOCUMENTS 0186118 7/1986 European Pat. Off. ............. 71/103

OTHER PUBLICATIONS

Webster's Ninth New Collegiate Dictionary, p. 1179, Merriam-Webster Inc., 1986.

*Primary Examiner*—Glennon H. Hollrah
*Assistant Examiner*—S. Trainor
*Attorney, Agent, or Firm*—Harry A. Pacini

[57] ABSTRACT

This invention embodies a two-part herbicidal system comprised of an acylated 1,3-dicarbonyl herbicide compound corresponding to the formula

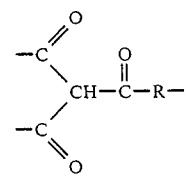

and tautomeric forms thereof where R is an aromatic moiety, optionally substituted, and a non-phytotoxic antidotally effective amount of an antidote therefor selected from the group of phenoxyalkanoic acids, including salts, esters and amides thereof for use on various crops.

6 Claims, No Drawings

HERBICIDAL COMPOSITIONS OF ACYLATED 1,3-DICARBONYL HERBICIDES AND PHENOXYALKANOIC ACIDS, SALTS, AMIDES AND ESTERS THEROF AS ANTIDOTES

FIELD OF THE INVENTION

This invention relates to herbicide compositions and methods of use, and more particularly, to certain herbicidal compositions comprising substituted acylated 1,3-dicarbonyl and 1,3,5-tricarbonyl compounds and as antidotes therefor substituted phenoxy alkanoic acids, their salts and esters, including amides.

BACKGROUND OF THE INVENTION

An herbicide is a compound which adversely controls or modifies plant growth, e.g., killing, retarding, defoliating, desiccating, bleaching, regulating, stunting, tillering, stimulating and dwarfing and otherwise adversely alter physiological plant processes. The term "plant" refers to all physical parts of a plant, including seeds, seedlings, saplings, roots, tubers, stems, stalks, foliage, and fruits. "Plant growth" includes all phases of development from seed germination to natural or induced cessation of life.

Herbicides are generally used to control or eradicate weed pests. They have gained a high degree of commercial success because it has been shown that such control can increase crop yield and reduce harvesting costs when weeds are not present in the field to complicate and reduce yield.

The most popular methods of herbicide application include: pre-plant incorporation into the soil; in-furrow application to seeds and surrounding soil; pre-emergence surface treatment of seeded soil; post-emergence treatment of the emerged and growing plant and soil; and pre-plant seed treatment. The preferred method of application is the post-emergence method whereby contact, translocation and residual herbicidal activity are in effect.

A manufacturer of an herbicide generally recommends a range of application rates and concentrations calculated to maximize weed control. The range of rates varies from approximately 0.01 to 50 pounds per acre (0.0111 to 56 kilograms per hectare [Kg/ha]), and is usually in the range of from 0.1 to 25 pounds per acre (0.112 to 28 Kg/ha). The term "herbicidally effective amount" describes an amount of an herbicide compound which adversely controls or modifies plant growth. The actual amount used depends upon several considerations, including particular weed susceptibility and overall cost limitations.

An important factor influencing the usefulness of a given herbicide is its selectivity towards crops. In some cases, a beneficial crop is susceptible to the effects of the herbicide. In addition, certain herbicidal compounds are phytotoxic to some weed species but not to others. To be effective, an herbicide must cause minimal damage (preferably no damage) to the beneficial crop while maximizing damage to weed species which infest the locus of the crop.

To preserve the beneficial aspects of herbicide use and to minimize crop damage, many herbicide antidotes have been prepared. These antidotes reduce or eliminate damage to the crop without substantially impairing the damaging effect of the herbicide on weed species. See, for example, U.S. Pat. Nos. 4,021,224, 4,021,229 and 4,230,874.

The precise mechanism by which an antidote reduces herbicidal crop injury has not been established. An antidote compound may be a remedy, interferent, protectant, or antagonist. As used herein, "antidote" describes a compound which has the effect of establishing herbicide selectivity, i.e., continue herbicidal phytotoxicity to weed species by the herbicide, and reduced or non-phytotoxicity to the cultivated crop species. The term "antidotally effective amount" describes an amount of an antidote compound which counteracts to some degree a phytotoxic response of a beneficial crop to an herbicide.

Acylated 1,3-dicarbonyl compounds have been found to be very effective herbicides with broad general herbicidal activity against a wide range of plant species. The method of controlling vegetation with the compounds comprises applying an herbicidally effective amount of the compounds, usually with an inert carrier, to the area where herbicidal control is desired. However, the herbicidal acylated 1,3-dicarbonyl compounds have been found in some instances to adversely affect or interfere with the cultivation of a variety of crops. Therefore, the effective use of these herbicides for controlling weeds in the presence of such crops is further enhanced by, or may require in many instances, the addition of an antidotally effective amount of a compound, which is antidotally effective with the herbicide.

DESCRIPTION OF THE INVENTION

It has now been discovered that certain compounds, broadly defined as aryloxyalkanoic acids, salts, amides or esters, when used in an antidotally effective amount are effective antidotes for the protection of a variety of crops from adverse herbicidal injury or the reduction of adverse herbicidal injury caused by the use of an herbicidally effective amount of an acylated 1,3-dicarbonyl carbocyclic or heterocyclic herbicidal compound.

DESCRIPTION OF THE HERBICIDE COMPOUNDS

The acylated 1,3-dicarbonyl herbicide compounds of this invention are contained within and correspond to the following general formula

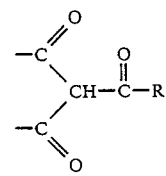

(A)

in which R is a group as hereinafter defined (and may generally be an optionally substituted aromatic moiety). Compounds of this type have been described in a number of references as being useful, for instance, as chemical intermediates and/or pesticides. The undefined remainder of the molecule represented in Formula A, which includes the dicarbonyl group, has a generally cyclical structure.

Acylated carbocyclic 1,3-dicarbonyl compounds of this type have the general structure

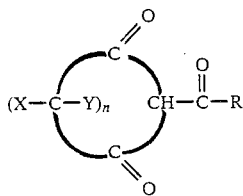
(B)

in which R is an optionally substituted aromatic moiety as hereinafter defined and n is 2 or 3, preferably 3. The ring can be unsubstituted (all X and Y groups are hydrogen), or one or more hydrogen atoms may be replaced by aliphatic, aromatic, heterocyclic or alkylene groups, particularly hydrocarbyl groups. Examples of such hydrocarbyl groups are alkyl, particularly lower alkyl, phenyl, and $C_2$–$C_5$ alkylene groups such as dimethylene, trimethylene and the like, in which case the compounds have a spiro structure. The carbocyclic ring may be saturated or unsaturated, containing an olefinic bond linking the 4- and 5-carbon atoms.

Acylated heterocyclic 1,3-dicarbonyl herbicide compounds of this invention have the general formula

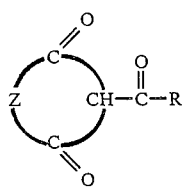
(I)

in which R is as defined herein and Z is a chain which contains 2 or 3 ring atoms, at least one of which is nitrogen, oxygen or sulfur. Nitrogen atoms in such rings may be unsubstituted or may be substituted by a $C_1$–$C_4$ alkyl group. Carbon atoms in such rings may be unsubstituted or may be substituted similarly to those in the carbocyclic compounds described above. Where possible, heterocyclic rings may be saturated or unsaturated.

Examples of heterocyclic 1,3-dicarbonyl structures include, for instance, barbituric acid derivatives, hydroxypyrones, 3,5-dioxotetrahydropyrans and thiopyrans, cyclical oxolactones, cyclical oxothiolactones and oxalactams.

One particular class of herbicide compounds is that in which the dicarbonyl compound is an optionally sustituted cyclohexanedione and the acylating group is a substituted benzoyl moiety. That is, R in Formula B above is substituted phenyl. In general, these compounds have the formula

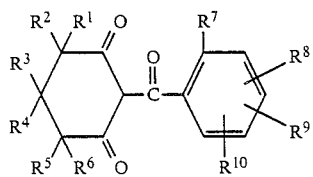
(II)

in which
$R^1$, $R^2$, $R^3$, $R^4$, $R^5$ and $R^6$ are independently hydrogen or $C_1$–$C_4$ alkyl or
$R^1$ or $R^3$ is

in which
$R_a$ is $C_1$–$C_4$ alkyl; phenyl, optionally substituted by from 2 to 5 methyl groups;
or in which $R^1$ and $R^2$, or $R^3$ and $R^4$, taken together are $C_2$–$C_5$ alkylene (such compounds have a spiro structure);
$R^7$ is halogen (chlorine, bromine, iodine or fluorine); cyano; $C_1$–$C_4$ alkyl; $C_1$–$C_4$ haloalkyl; $R_kSO_n$ in which $R_k$ is $C_1$–$C_4$ alkyl and n=0, 1 or 2; $C_1$–$C_4$ alkoxy; or nitro;
$R^8$, $R^9$ and $R^{10}$ independently are hydrogen or substituents including halogen; $C_1$–$C_4$ alkyl; $C_1$–$C_4$ alkoxy, trifluoromethoxy; cyano; nitro; $C_1$–$C_4$ haloalkyl; $C_1$–$C_4$ alkylthio; phenoxy; or substituted phenoxy in which the substituent is halogen or halomethyl or both;
$R_bS(O)_n$ in which n is 0, 1 or 2; and $R_b$ is $C_1$–$C_4$ alkyl, $C_1$–$C_4$ haloalkyl, phenyl or benzyl,

in which $R_c$ is $C_1$–$C_4$ alkyl,
—$NR_dR_e$ in which $R_d$ and $R_e$ independently are hydrogen or $C_1$–$C_4$ alkyl;
$R_fC(O)$— in which $R_f$ is hydrogen, $C_1$–$C_4$ alkyl, $C_1$–$C_4$ haloalkyl or $C_1$–$C_4$ alkoxy;
$SO_2NR_gR_h$ in which $R_g$ and $R_h$ independently are hydrogen or $C_1$–$C_4$ alkyl;
or $R^8$ and $R^9$ taken together form a ring structure with two adjacent carbon atoms of the phenyl ring to which they are attached.

Compounds of this type, with various substituents on either or both of the cyclohexane or phenyl rings are disclosed in: European Patent Application, Publication No. 90262; the following copending United States patent applications, assigned to the Assignee herewith, and entitled "Certain 2-(2-Substituted Benzoyl)-1,3-Cyclohexanediones", Ser. No. 634,408, filed July 31, 1984; Ser. No. 640,791, filed Aug. 17, 1984; Ser. No. 752,702, filed July 8, 1985; and Ser. No. 722,593, filed Sept. 5, 1985; the following U.S. patent applications assigned to the Assignee hereof, Ser. No. 683,900, filed Dec. 20, 1984 and Ser. No. 802,135, filed Nov. 29, 1985, entitled "Certain 2-(2 Nitrobenzoyl)-1,3-Cyclohexanediones"; Ser. No. 683,899, filed Dec. 20, 1984, entitled "Certain 2-(2'-Cyanobenzoyl)-1,3-Cyclohexanediones"; Ser. No. 683,898, filed Dec. 20, 1984 and Ser. No. 802,133, filed Nov. 29, 1985, entitled "Certain 2-(2'-Substituted Benzoyl)-1,3-Cyclohexanediones"; Ser. No. 683,884, filed Dec. 20, 1984 and Ser. No. 802,134, filed Nov. 29, 1985, entitled "Certain 2-(2'-Alkylbenzoyl)-1,3-Cyclohexanediones". The disclosures of these documents are hereby incorporated herein.

Some specific types of such acylated heterocyclic 1,3-dicarbonyl herbicide compounds include:
barbituric acid derivatives such as those of the formula IV

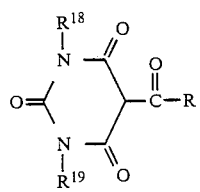 (IV)

in which $R^{18}$ and $R^{19}$ are hydrogen or $C_1-C_4$ alkyl and R is substituted phenyl such as

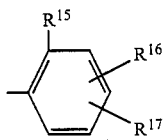

in which $R^{15}$, $R^{16}$ and $R^{17}$ are as defined hereinafter. Such compounds are described, for instance, in copending, commonly assigned U.S. patent application No. 872,068, filed June 9, 1986; entitled "Certain S-(2-Substituted Benzoyl)-Barbituric Acids", the disclosure of which is hereby incorporated herein;

oxolactams such as those having the formula V

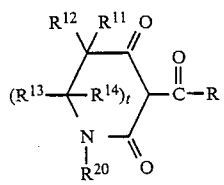 (V)

in which $R^{11}-R^{14}$ and $R^{20}$ are independently hydrogen or $C_1-C_4$ alkyl, or $R^{11}$ and $R^{12}$ together are $C_2-C_5$ alkylene, t is 0 or 1 and R is substituted phenyl such as

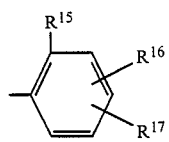

in which $R^{15}$ is hydrogen; halogen; $C_1-C_2$ alkyl; $C_1-C_2$ alkoxy; nitro; cyano; $C_1-C_2$ haloalkyl; or $R_mSO_n$ wherein $R_m$ is $C_1-C_2$ alkyl and n is 0, 1 or 2; trifluoromethyl or difluoromethyl; or trifluoromethoxy or difluoromethoxy. Preferably $R^{15}$ is chlorine, bromine, $C_1-C_2$ alkyl, $C_1-C_2$ alkoxy, trifluoromethyl, cyano, nitro, $C_1-C_2$ alkyl, $C_1-C_2$ alkoxy, trifluoromethyl, cyano, nitro, $C_1-C_2$ alkylthio or $C_1-C_2$ alkylsulfonyl; and $R^{16}$ and $R^{17}$ independently are (1) hydrogen, (2) halogen; (3) $C_1-C_4$ alkyl; (4) $C_1-C_4$ alkoxy; (5) trifluoromethoxy; (6) cyano; (7) nitro; (8) $C_1-C_4$ alkyl; (9) $R^bSO_n$— wherein n is the integer 0, 1 or 2; and $R^b$ is (a) $C_1-C_4$ alkyl; (b) $C_1-C_4$ alkyl substituted with halogen or cyano; (c) phenyl; or (d) benzyl. Such compounds are disclosed, for instance, in copending, commonly assigned U.S. application No. 871,973, filed June 9, 1986, entitled "Certain 3-(Benzoyl-4-Oxolactams" the disclosure of which is hereby incorporated by reference;

Herbicidal oxolactones and oxothiolactones within this invention such as those having the formula VI

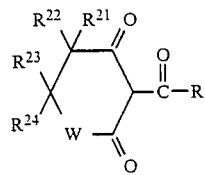 (VI)

in which $R^{21}-R^{24}$ are independently hydrogen or $C_1-C_4$ alkyl; or $R_{21}$ and $R_{22}$ together are $C_2-C_5$ alkylene; or $R^{23}$ and $R^{24}$ together are $C_2-C_5$ alkylene; or $R^{21}$ and $R^{23}$ together form a bond, and R is substituted phenyl such as

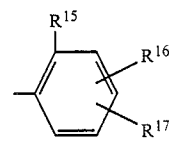

in which $R^{15}-R^{17}$ are as defined above; and W is oxygen or sulfur. When $R^{21}$ and $R^{23}$ together form a bond, the compounds contain an unsaturated heterocyclic ring. Such compounds are disclosed, for instance, in copending commonly assigned U.S. application No. 871,975, filed June 9, 1986; entitled "Certain 4-Oxo-Benzoyl-Valerolactones and Thiolactones", the disclosure of which is hereby incorporated herewith;

dioxotetrahydropyrans and -thiopyrans such as those having the formula VII

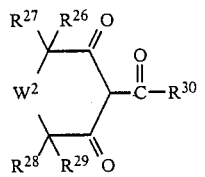 (VII)

in which $R^{26}-R^{29}$ are independently hydrogen or $C_1-C_4$ alkyl or $R^{26}$ and $R^{27}$ together are $C_2-C_5$ alkylene, or $R^{28}$ and $R^{29}$ together are $C_2-C_5$ alkylene; $W^2$ is oxygen, sulfur or sulfonyl and $R^{30}$ is substituted phenyl such as

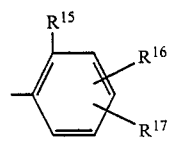

in which $R^{15}-R^{17}$ are as previously defined. Such compounds are described, for instance, in copending, commonly assigned U.S. application Ser. No. 872,080, filed Sept. 9, 1986, entitled "Certain Substituted 4-Benzoyl-3,5-Oxo-tetrahydropyrans and Thiopyrans".

Another embodiment of this invention is an herbicidal composition comprising a 2-(2-substituted benzoyl)-4-(substituted or unsubstituted phenyl) cyclohexanedione and an antidote with an inert carrier therefor. The 1,3-cyclohexanedione moiety is preferably substituted with groups hereinafter defined. The benzoyl and cyclohexanedione moieties can be further substituted.

Within the scope of this embodiment are compounds in which R in Formula B above is a substituted phenyl. In general, these compounds have the formula VIII:

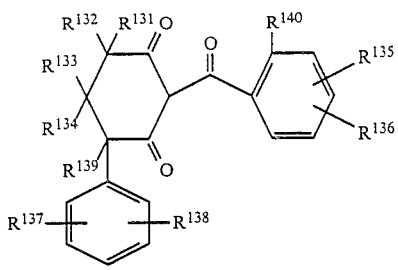

wherein
$R^{140}$ is halogen; $C_1$-$C_2$ alkyl; $C_1$-$C_2$ alkoxy; trifluoromethoxy; or difluoromethoxy; nitro; cyano; $C_1$-$C_2$ haloalkyl; $R^aSO_n$— wherein n is 0 or 2; and $R^a$ is $C_1$-$C_2$ alkyl; trifluoromethyl or difluoromethyl. Of particular interest are compounds in which $R^{140}$ is chlorine, bromine, $C_1$-$C_2$ alkyl, $C_1$-$C_2$ alkoxy, trifluoromethyl, cyano, nitro, $C_1$-$C_2$ alkylthio or $C_1$-$C_2$ alkylsulfonyl; more preferably chlorine, nitro, methyl, trifluormethyl or methylsulfonyl; and $R^{131}$ is hydrogen or $C_1$-$C_4$ alkyl;
$R^{132}$ is hydrogen or $C_1$-$C_4$ alkyl;
$R^{131}$ and $R^{132}$ together are $C_2$-$C_5$ alkylene;
$R^{133}$ is hydrogen or $C_1$-$C_4$ alkyl;
$R^{134}$ is hydrogen or $C_1$-$C_4$ alkyl;
$R^{133}$ and $R^{134}$ together are $C_2$-$C_5$ alkylene;
$R^{135}$, $R^{136}$, $R^{137}$ and $R^{138}$ independently are (1) hydrogen; (2) chlorine, fluorine or bromine; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$— wherein n is the integer 0, 1 or 2; and
$R^b$ is (a) $C_1$-$C_4$ alkyl;
(b) $C_1$-$C_4$ alkyl substituted with halogen or cyano;
(c) phenyl; or
(d) benzyl;
(10) —$NR^cR^d$ wherein
$R^c$ and $R^d$ independently are hydrogen or $C_1$-$C_4$ alkyl;
(11) $R^eC(O)$— wherein $R^e$ is $C_1$-$C_4$ alkyl or $C_1$-$C_4$ alkoxy; (12) —$SO_2NR^cR^d$ wherein $R^c$ and $R^d$ are as defined; or (13) —$N(R^c)C(O)R^d$ wherein $R^e$ and $R^d$ are as defined; and
$R^{139}$ is hydrogen or $C_1$-$C_4$ alkyl.

Preferably $R^{135}$ is in the 3-position and $R^{135}$ and $R^{137}$ are hydrogen, chlorine, fluorine, trifluoromethyl, cyano, $C_1$-$C_4$ alkoxy or $C_1$-$C_4$ thioalkyl; or $R^{135}$ and $R^{137}$ are hydrogen and $R^{136}$ and $R^{138}$ are in the 4-position; wherein $R^{136}$ and $R^{138}$ are halogen, cyano, trifluoromethyl, or $R^bSO_2$ wherein $R^b$ is $C_1$-$C_4$ alkyl or $C_1$-$C_4$ haloalkyl.

Compounds of this type are described in copending U.S. application Ser. No. 906,462, filed Sept. 12, 1986.

Another embodiment of this invention is an herbicidal composition comprising an herbicidally active 2-(substituted benzoyl)-cyclohexanedione-1,3 and the acylating group is a substituted benzoyl moiety and an antidote with an inert carrier therefor. The 4- and 6-positions of the cyclohexanedione-1,3 moiety are preferably substituted with groups hereinafter defined, most preferably with hydrogen or methyl groups. The substituted benzoyl and cyclohexanedione-1,3 moieties can be further substituted.

Within the scope of this embodiment are the compounds in which R in Formula B, above, is substituted phenyl. In general, these compounds have the formula IX:

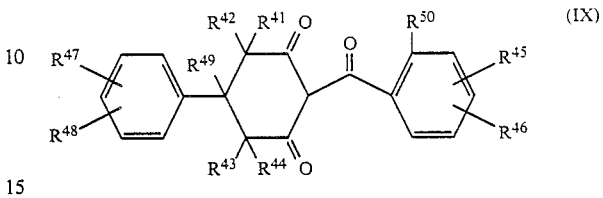

wherein
$R^{50}$ is halogen; $C_1$-$C_2$ alkyl; $C_1$-$C_2$ alkoxy; trifluoromethoxy or difluoromethoxy; nitro; cyano; $C_1$-$C_2$ haloalkyl; $R^aSO_n$— wherein n is 0 or 2; and $R^a$ is $C_1$-$C_2$ alkyl; trifluoromethyl; or difluoromethyl; and
$R^{41}$ is hydrogen or $C_1$-$C_4$ alkyl;
$R^{42}$ is hydrogen or $C_1$-$C_4$ alkyl;
$R^{41}$ and $R^{42}$ together are $C_2$-$C_5$ alkylene;
$R^{43}$ is hydrogen or $C_1$-$C_4$ alkyl;
$R^{44}$ is hydrogen or $C_1$-$C_4$ alkyl;
$R^{43}$ and $R^{44}$ together are $C_2$-$C_5$ alkylene;
$R^{45}$, $R^{46}$, $R^{47}$ and $R^{48}$ independently are (1) hydrogen; (2) halogen selected from the group consisting of chlorine, fluorine or bromine; (3) $C_1$ $C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$— wherein n is the integer 0, 1 or 2; and
$R^b$ is (a) $C_1$-$C_4$ alkyl;
(b) $C_1$-$C_4$ alkyl substituted with halogen or cyano;
(c) phenyl; or
(d) benzyl;
(10) —$NR^cR^d$ wherein
$R^c$ and $R^d$ independently are hydrogen or $C_1$-$C_4$ alkyl;
(11) $R^eC(O)$— wherein $R^e$ is $C_1$-$C_4$ alkyl or $C_1$-$C_4$ alkoxy; (12) —$SO_2NR^cR^d$ wherein $R^c$ and $R^d$ are as defined; or (13) —$N(R^c)C(O)R^d$ wherein $R^e$ and $R^d$ are as defined; and
$R^{49}$ is hydrogen or $C_1$-$C_4$ alkyl.

Of particular interest are compounds in which $R^{45}$ is in the 3-position and $R^{45}$ is hydrogen, chlorine, fluorine, trifluoromethyl, cyano, $C_1$-$C_4$ alkoxy or $C_1$-$C_4$ thioalkyl; or $R^{45}$ is hydrogen; or $R^{46}$ is in the 4-position; and $R^{46}$ is halogen, cyano, trifluoromethyl, or $R^bSO_2$ wherein $R^b$ is $C_1$-$C_4$ alkyl, preferably methyl or $C_1$-$C_4$ haloalkyl, difluoromethyl or trifluoromethyl.

Compounds of this type are described in copending U.S. patent application Ser. No. 906,461, filed Sept. 12, 1986.

Another embodiment of this invention is an herbicidal composition comprising an herbicidally active 2-(2-substituted benzoyl)-4-(substituted oxy or substituted thio)-1,3-cyclohexanedione and an antidote with an inert carrier therefor. The 5- and 6-positions of the 1,3-cyclohexanedione moiety are preferably substituted with groups hereinafter defined, most preferably with hydrogen or methyl groups. The substituted benzoyl and cyclohexanedione moieties can be further substituted.

Within the scope of this embodiment are compounds having the following structural formula

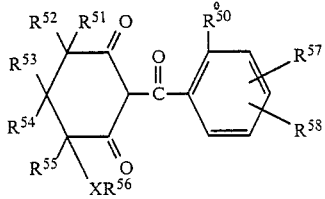 (X)

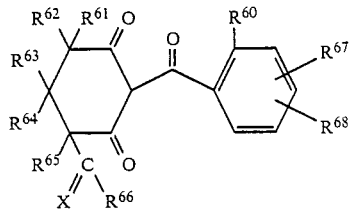 (XI)

wherein

X is oxy, thio, sulfinyl or sulfonyl;

$R^{50}$ is halogen; $C_1$-$C_2$ alkyl; $C_1$-$C_2$ alkoxy, preferably methoxy; trifluoromethoxy; difluoromethoxy; nitro; cyano; $C_1$-$C_2$ haloalkyl; $R^aSO_n$— wherein n is 0 or 2, preferably 2 and $R^a$ is $C_1$-$C_2$ alkyl; trifluoromethyl or difluoromethyl. Preferably, $R^{50}$ is chlorine, bromine, $C_1$-$C_2$ alkyl, $C_1$-$C_2$ alkoxy, trifluoromethyl, cyano, nitro, $C_1$-$C_2$ alkylthio or $C_1$-$C_2$ alkylsulfonyl; more preferably chlorine, nitro, methyl, trifluoromethyl or methylsulfonyl;

$R^{51}$ is hydrogen; $C_1$-$C_4$ alkyl; phenyl; or substituted phenyl;

$R^{52}$ is hydrogen or $C_1$-$C_4$ alkyl; or $R^{51}$ and $R^{52}$ together are $C_2$-$C_5$ alkylene;

$R^{53}$ is hydrogen; $C_1$-$C_4$ alkyl; phenyl; or substituted phenyl with the proviso that $R^{51}$ and $R^{53}$ are not both phenyl or substituted phenyl;

$R^{54}$ is hydrogen or $C_1$-$C_4$ alkyl;

$R^{55}$ is hydrogen or $C_1$-$C_4$ alkyl;

$R^{56}$ is hydrogen, $C_1$-$C_4$ alkyl, $C_1$-$C_4$ haloalkyl, or phenyl and $R^{57}$ and $R^{58}$ independently are (1) hydrogen; (2) halogen; (3) $C_1$-$C_4$ alkyl; (4) $C_1$-$C_4$ alkoxy; (5) trifluoromethoxy; (6) cyano; (7) nitro;

(8) $C_1$-$C_4$ haloalkyl; (9) $R^bSO_n$— wherein n is the integer 0, 1 or 2; and $R^b$ is (a) $C_1$-$C_4$ alkyl;

(b) $C_1$-$C_4$ alkyl substituted with halogen or cyano;

(c) phenyl; or (d) benzyl;

(10) —$NR^cR^d$ wherein $R^c$ and $R^d$ independently are hydrogen or $C_1$-$C_4$ alkyl; (11) $R^eC(O)$— wherein $R^e$ is $C_1$-$C_4$ alkyl or $C_1$-$C_4$ alkoxy; (12) —$SO_2NR^cR^d$ wherein $R^c$ and $R^d$ are as defined; or (13) —$N(R^c)C(O)R^d$ wherein $R^c$ and $R^d$ are as defined.

Compounds of this type are described in copending U.S. patent application Ser. No. 919,280, filed Oct, 16, 1986.

Another embodiment of this invention is an herbicidal composition comprising an herbicidally active 2-(2-substituted benzoyl)-4-(substituted imino, oximino or carbonyl)-1,3-cyclohexanedione and an antidote with an inert carrier therefor. The 5- and 6-positions of the 1,3-cyclohexanedione moiety are substituted with groups hereinafter defined, preferably with hydrogen or methyl groups. The benzoyl and imino, oximino or carbonyl moieties can be substituted.

Also embodied within the scope of this invention are novel compounds having the following structural formula wherein X is oxygen or $NR^{69}$ wherein $R^{69}$ is hydrogen, $C_1$-$C_4$ alkyl, or $C_1$-$C_4$ alkoxy;

$R^{60}$ is halogen; $C_1$-$C_2$ alkyl; $C_1$-$C_2$ alkoxy; trifluoromethoxy or difluoromethoxy; nitro; cyano; $C_1$-$C_2$ haloalkyl; $R^aSO_n$— wherein n is 0 or 2; and $R^a$ is $C_1$-$C_2$ alkyl; trifluoromethyl; or difluoromethyl. Preferably, $R^{60}$ is chlorine, bromine, $C_1$-$C_2$ alkyl, $C_1$-$C_2$ alkoxy, trifluorometyl, cyano, nitro, $C_1$-$C_2$ alkylthio or $C_1$-$C_2$ alkylsulfonyl; more preferably chlorine, nitro, methyl, trifluoromethyl or methylsulfonyl; and $R^{61}$ is hydrogen; $C_1$-$C_4$ alkyl; phenyl; or substituted phenyl;

$R^{62}$ is hydrogen or $C_1$-$C_4$ alkyl; or $R^{61}$ and $R^{62}$ together are $C_2$-$C_5$ alkylene;

$R^{63}$ is hydrogen; $C_1$-$C_4$ alkyl; phenyl; or substituted phenyl, with the proviso that $R^{61}$ and $R^{63}$ are not both phenyl or substituted phenyl;

$R^{64}$ is hydrogen or $C_1$-$C_4$ alkyl;

$R^{65}$ is hydrogen or $C_1$-$C_4$ alkyl;

$R^{66}$ is $C_1$-$C_4$ alkyl or $C_1$-$C_4$ haloalkyl;

$R^{67}$ and $R^{68}$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl, preferably trifluoromethyl; (9) $R^bSO_n$— wherein n is the integer 0, 1 or 2, preferably 2; and $R^b$ is (a) $C_1$-$C_4$ alkyl;

(b) $C_1$-$C_4$ alkyl substituted with halogen or cyano;

(c) phenyl; or (d) benzyl;

(10) —$NR^cR^d$ wherein $R^c$ and $R^d$ independently are hydrogen or $C_1$-$C_4$ alkyl; (11) $R^eC(O)$— wherein $R^e$ is $C_1$-$C_4$ alkyl or $C_1$-$C_4$ alkoxy; (12) $SO_2NR^cR^d$ wherein $R^c$ and $R^d$ are as defined; or (13) —$N(R^c)C(O)R^d$ wherein $R^c$ and $R^d$ are as defined.

Within this embodiment, preferably $R^{67}$ is in the 3-position and $R^{67}$ is hydrogen, chlorine, fluorine, trifluoromethyl, cyano, $C_1$-$C_4$ alkoxy or $C_1$-$C_4$ thioalkyl; and preferably $R^{68}$ is in the 4-position and $R^{68}$ is halogen, cyano, trifluoromethyl, or $R^bSO_2$ wherein $R^b$ is $C_1$-$C_4$ alkyl, or $C_1$ haloalkyl, preferably chloromethyl, difluoromethyl or trifluoromethyl.

Compounds of this type are described in copending U.S. patent application Ser. No. 919,278, filed Oct. 16, 1986.

Another embodiment of this invention is an herbicidal composition comprising an herbicidally active 2-(2-substituted benzoyl)-4-(substituted)-1,3-cyclohexanedione and an antidote with an inert carrier therefor. The 5- and 6-positions and the 4-position of the 1,3-cyclohexanedione moiety are preferably substituted with groups hereinafter defined, most preferably with halogen or methyl groups. The benzoyl moiety can be substituted, with the groups as hereinafter recited.

Within the scope of this embodiment are compounds having the following structural formula

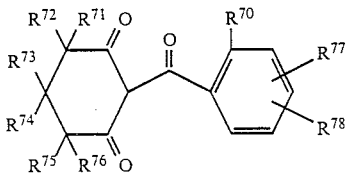

(XII)

wherein $R^{70}$ is halogen; $C_1$-$C_2$ alkyl; $C_1$-$C_2$ alkoxy; trifluoromethoxy; diflouromethoxy; nitro; cyano; $C_1$-$C_2$ haloalkyl; $R^aSO_n$— wherein n is 0 or 2; and $R^a$ is $C_1$-$C_2$ alkyl; trifluoromethyl or difluoromethyl. Preferably, $R^{70}$ is chlorine, bromine, $C_1$-$C_2$ alkyl, $C_1$-$C_2$ alkoxy, trifluoromethyl, cyano, nitro, $C_1$-$C_2$ alkylthio or $C_1$-$C_2$ alkylsulfonyl; more preferably chlorine, nitro, methyl, trifluoromethyl or methylsulfonyl; and $R^{71}$ is hydrogen; $C_1$-$C_4$ alkyl; halogen; phenyl; or substituted phenyl;

$R^{72}$ is hydrogen or $C_1$-$C_4$ alkyl; or $R^{71}$ and $R^{72}$ together are $C_2$-$C_5$ alkylene;

$R^{73}$ is hydrogen; $C_1$-$C_4$ alkyl; phenyl; or substituted phenyl, with the proviso that $R^{71}$ and $R^{73}$ are not both phenyl or substituted phenyl;

$R^{74}$ is hydrogen or $C_1$-$C_4$ alkyl;

$R^{75}$ is hydrogen, halogen or $C_1$-$C_4$ alkyl;

$R^{76}$ is halogen, nitro, cyano, trifluoromethyl; —C(O)$NR_2^b$ wherein $R^b$ is hydrogen or $C_1$-$C_2$ alkyl; and $R^{77}$ and $R^{78}$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$— wherein n is the integer 0, 1 or 2; and $R^b$ is (a) $C_1$-$C_4$ alkyl;
(b) $C_1$-$C_4$ alkyl substituted with halogen or cyano;
(c) phenyl; or
(d) benzyl;
(10) —$NR^cR^d$ wherein $R^c$ and $R^d$ independently are hydrogen or $C_1$-$C_4$ alkyl; (11) $R^eC(O)$— wherein $R^e$ is $C_1$-$C_4$ alkyl or $C_1$-$C_4$ alkoxy; (12) —$SO_2NR^cR^d$ wherein $R^c$ and $R^d$ are as defined; or (13) —$N(R^c)C(O)R^d$ wherein $R^c$ and $R^d$ are as defined.

Within this embodiment, preferably $R^{77}$ is in the 3-position and $R^{77}$ is hydrogen, chlorine, fluorine, trifluoromethyl, cyano, $C_1$-$C_4$ alkoxy or $C_1$ $C_4$ thioalkyl; preferably $R^{78}$ is in the 4-position and $R^{78}$ is halogen, cyano, trifluoromethyl, or $R^bSO_2$ wherein $R^b$ is $C_1$-$C_4$ alkyl, or $C_1$-$C_4$ haloalkyl, preferably chloromethyl, difluoromethyl or trifluoromethyl.

Compounds of this type are described in copending U.S. patent application Ser. No. 919,277, filed Oct. 16, 1986.

The term "$C_1$-$C_4$ alkyl" includes methyl, ethyl, n-propyl, isopropyl, n-butyl, sec-butyl, isobutyl and t-butyl. The term "halogen" includes chlorine, bromine, iodine and fluorine. The terms "$C_1$-$C_4$ alkoxy" includes methoxy, ethoxy, n-propoxy, isopropoxy, n-butoxy, sec-butoxy, isobutoxy and t-butoxy. The term "$C_1$-$C_4$ haloalkyl" includes the alkyl groups defined above under $C_1$-$C_4$ alkyl in which on or more hydrogens is replaced by chlorine, bromine, iodine or fluorine.

Salts of the above-described compounds are included within the scope of the instant invention.

One method for production of acylated dicarbonyl compounds is disclosed in European Patent Application, Publication No. 186,117.

The following is a list of sample compounds as found in the above description of active herbicides.

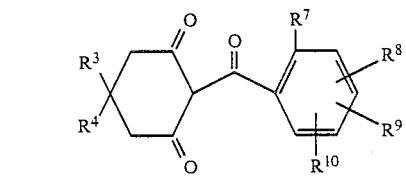

| Cmpd. No. | R3 | $R^4$ | $R^7$ | $R^8$ | $R^9$ | $R^{10}$ |
|---|---|---|---|---|---|---|
| 51A | H | H | Cl | H | 4-$CH_3SO_2$— | H |
| 55A | $CH_3$ | $CH_3$ | Cl | H | 4-$CH_3SO_2$— | H |
| 90A | H | H | Cl | 3-$C_2H_5O$ | 4-$C_2H_5SO_2$ | H |

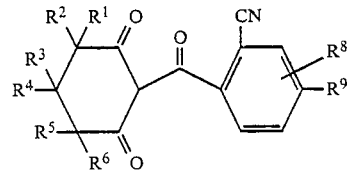

| Comp. No. | $R^1$ | $R^2$ | $R^3$ | $R^4$ | $R^5$ | $R^6$ | $R^8$ | $R^9$ |
|---|---|---|---|---|---|---|---|---|
| 1C | $CH_3$ | $CH_3$ | H | H | H | H | H | H |

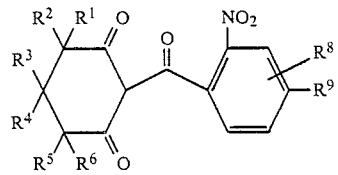

-continued

| Comp. No. | R¹ | R² | R³ | R⁴ | R⁵ | R⁶ | R⁸ | R⁹ |
|---|---|---|---|---|---|---|---|---|
| 4D | CH₃ | CH₃ | H | H | H | H | H | H |
| 8D | H | H | H | H | H | H | H | CF₃ |
| 24D | CH₃ | CH₃ | H | H | H | H | H | SO₂CH₃ |
| 70D | H | H | H | H | CH₃ | CH₃ | H | SO₂CH₂Cl |

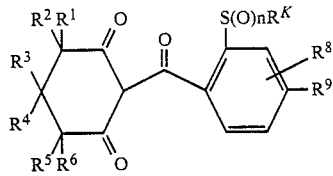

| Comp. No. | n | R^K | R¹ | R² | R³ | R⁴ | R⁵ | R⁶ | R⁸ | R⁹ |
|---|---|---|---|---|---|---|---|---|---|---|
| 4E | 2 | CH₃ | CH₃ | CH₃ | H | H | CH₃ | H | H | H |
| 16E | 0 | CH₃ | H | H | H | H | H | H | H | —SO₂n-C₃H₇ |

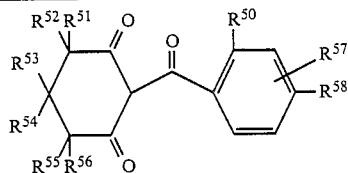

| Comp. No. | R⁵⁰ | R⁵¹ | R⁵² | R⁵³ | R⁵⁴ | R⁵⁵ | R⁵⁶ | R⁵⁷ | R⁵⁸ |
|---|---|---|---|---|---|---|---|---|---|
| 8F | CH₃ | CH₃ | CH₃ | H | H | CH₃ | H | H | CH₃SO₂— |
| 29F | CF₃ | H | H | H | H | H | H | H | C₂H₅S— |
| 36F | CH₃ | H | H | H | H | H | H | 3-Cl | C₂H₅SO₂ |
| 50F | CF₃ | CH₃ | CH₃ | H | H | H | H | H | CF₃ |

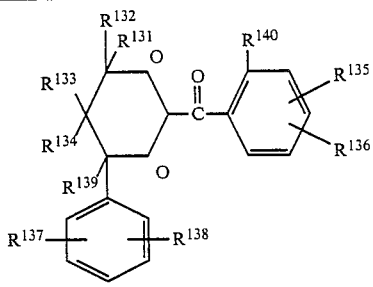

| Cmpd. No. | R¹⁴⁰ | R¹³¹ | R¹³² | R¹³³ | R¹³⁴ | R¹³⁵ | R¹³⁶ | R¹³⁷ | R¹³⁸ | R¹³⁹ |
|---|---|---|---|---|---|---|---|---|---|---|
| VIII-14 | Cl | H | H | Me | H | H | 4-SO₂Me | 2-F | H | H |
| VIII-17 | NO₂ | H | H | H | H | H | 4-Cl | 2-F | H | Me |
| VIII-24 | Cl | H | H | H | H | H | 4-SO₂Me | H | H | H |

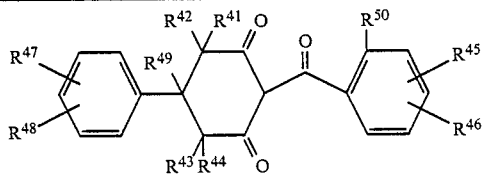

| Comp. No. | R⁵⁰ | R⁴¹ | R⁴² | R⁴³ | R⁴⁴ | R⁴⁵ | R⁴⁶ | R⁴⁷ | R⁴⁸ | R⁴⁹ |
|---|---|---|---|---|---|---|---|---|---|---|
| II-4 | Cl | CH₃ | CH₃ | H | H | H | 4-SO₂CH₃ | H | H | H |
| II-6 | NO₂ | H | H | H | H | H | 4-Cl | H | H | H |

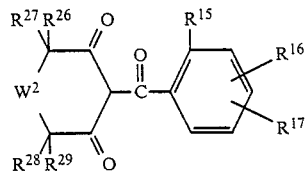

-continued

| Cmpd No | $R^{15}$ | $R^{26}$ | $R^{27}$ | $R^{28}$ | $R^{29}$ | $R^{16}$ | $R^{17}$ | $W^2$ |
|---|---|---|---|---|---|---|---|---|
| VII-1 | $NO_2$ | $CH_3$ | $CH_3$ | H | H | H | 4-Cl | O |
| VII-5 | Cl | H | H | H | H | H | 4-Cl | S |
| VII-7 | Cl | $CH_3$ | H | $CH_3$ | H | H | 4-Cl | S |

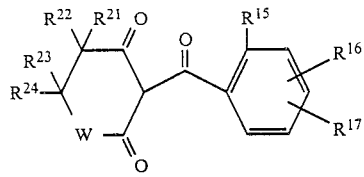

| Comp. No. | $R^{15}$ | $R^{21}$ | $R^{22}$ | $R^{23}$ | $R^{24}$ | $R^{16}$ | $R^{17}$ | W |
|---|---|---|---|---|---|---|---|---|
| VI-1 | Cl | H | $CH_3$ | bond | | H | 4-Cl | O |
| VI-4 | $NO_2$ | H | $CH_3$ | H | H | H | H | O |
| VI-9 | $NO_2$ | H | $CH_3$ | H | $CH_3$ | H | 4-Cl | O |
| VI-21 | Cl | H | $CH_3$ | H | $CH_3$ | H | 4-$SO_2CH_3$ | S |

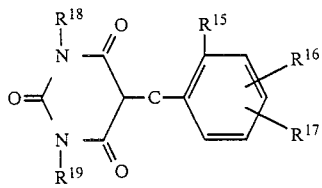

| Cmpd. No. | $R^{15}$ | $R^{18}$ | $R^{19}$ | $R^{16}$ | $R^{17}$ |
|---|---|---|---|---|---|
| IV-1 | Cl | $CH_3$ | $CH_3$ | H | 4-Cl |
| IV-6 | $NO_2$ | $CH_3$ | $CH_3$ | H | H |

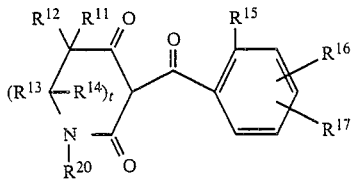

| Comp. No. | $R^{15}$ | $R^{11}$ | $R^{12}$ | $R^{13}$ | $R^{14}$ | $R^{16}$ | $R^{17}$ | $R^{20}$ | t |
|---|---|---|---|---|---|---|---|---|---|
| V-1 | $NO_2$ | H | H | H | H | H | 4-Cl | n-$C_3H_7$ | 1 |
| V-2 | $NO_2$ | H | H | n/a | n/a | H | 4-Cl | n-$C_3H_7$ | 0 |
| V-3 | Cl | H | H | H | H | H | 4-$SO_2CH_3$ | n-$C_3H_7$ | 1 |
| V-7 | $NO_2$ | H | H | $CH_3$ | $CH_3$ | H | 4-Cl | $CH_3$ | 1 |
| V-15 | $NO_2$ | $CH_3$ | H | H | H | H | 4-$SO_2CH_3$ | $C_2H_5$ | 1 |

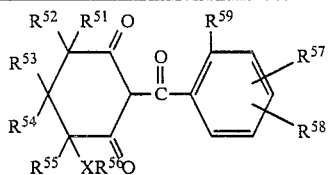

| Comp. No. | $R^{59}$ | $R^{51}$ | $R^{52}$ | $R^{53}$ | $R^{54}$ | $R^{55}$ | X | $R^{56}$ | $R^{57}$ | $R^{58}$ |
|---|---|---|---|---|---|---|---|---|---|---|
| X-5 | Cl | H | H | H | H | H | S | $CH_3$ | H | 4-$SO_2CH_3$ |
| X-6 | $NO_2$ | $CH_3$ | H | H | H | H | $SO_2$ | $CH_3$ | H | 4-Cl |
| X-13 | $NO_2$ | H | H | H | H | $CH_3$ | S | $CH_3$ | H | H |

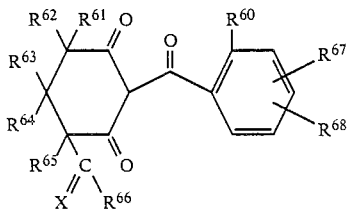

| Cmpd. No. | $R^{60}$ | $R^{61}$ | $R^{62}$ | $R^{63}$ | $R^{64}$ | $R^{65}$ | $R^{66}$ | $R^{67}$ | $R^{68}$ | X |
|---|---|---|---|---|---|---|---|---|---|---|
| XI-1 | Cl | H | H | H | H | H | $CH_3$ | H | 4-$SO_2CH_3$ | $C_2H_5$—ON |

-continued

| | | | | | | | | | |
|---|---|---|---|---|---|---|---|---|---|
| XI-6 | Cl | H | H | H | H | H | CH₃ | 3-Cl | 4-SO₂C₂H₅ CH₃—ON |
| XI-7 | NO₂ | H | H | H | H | H | CH₃ | H | 4-Cl CH₃—ON |
| XI-8 | Cl | H | H | H | H | H | CF₃ | H | 4-Cl CH₃—ON |

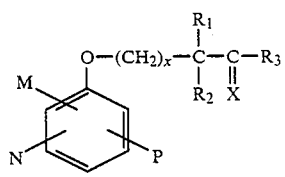

| Cmpd. No. | $R^{70}$ | $R^{71}$ | $R^{72}$ | $R^{73}$ | $R^{74}$ | $R^{75}$ | $R^{76}$ | $R^{77}$ | $R^{78}$ |
|---|---|---|---|---|---|---|---|---|---|
| XII-1 | Cl | H | H | H | H | H | Br | H | 4-SO₂CH₃ |
| XII-6 | NO₂ | CH₃ | CH₃ | H | H | H | Br | H | H |
| XII-7 | Cl | H | H | H | H | H | Cl | H | 4-Cl |
| XII-9 | NO₂ | H | H | CH₃ | CH | H | F | H | 4-CF₃ |

DESCRIPTION OF ANTIDOTES

The phenoxyalkanoic acids are the best known and most widely available of this class of compound. Normally, they are widely used for their selective weed killing properties, but sublethal doses are used as growth regulators to promote fruit set and for thinning. The most notable of the class are 2,4-dichlorophenoxy acetic acid (2,4-D), its esters, amides and salts; 2,4,5-trichlorophenoxy acetic acid (2,4,5-T), its esters, amides and salts; and (4-chloro-o-tolyloxy)acetic acid (4-CPA). Further examples of the various salts and esters are: sodium salt, potassium salt, ammonium salt, triethylamine salt, triethanolamine salt, the alkyl ester, such as butyl ester, butoxyethanol ester, propyleneglycolbutylether ester, and tetrahydrofurfuryl ester. Also of interest, in place of the phenoxy acetic acid portion or grouping the alpha- and beta-phenoxyproprionic acid, alpha- and beta-phenoxybutyric acid, or higher analog may be substituted.

The chlorophenoxy compounds described above have profound effects upon the growth and structure of plants when used in an herbicidally effective amount. Various disruptions such as epinastic bending, formation of tumors, cessation in the division of the meristematic cells, elongating cells stop length growth but continue radial expansion, phytosynthesis is inhibited and other hormonal imbalanced effects caused by the herbicide, the imbalance could be in the auxin-kinin relation.

This invention embodies a two-part herbicidal system comprised of (a) an herbicide as described hereinabove and (b) an effective antidote therefor. It has been found that such preferred antidote compounds within the instant invention are selected from the general class of chemical substances known and described above as aryloxyalkanoic acids and their derivatives, which have been found to be effective as herbicide antidotes for the above-described acylated 1,3-dicarbonyl herbicides. The preferred compositions of this invention may include any one or more of such antidotes with the described herbicides. The variety of crops on which the above-described herbicides is useful can be significantly broadened by the use of an antidote to protect one or more crops from injury therefrom and render the composition more selective against weeds. Some of the preferred antidotes are the di- and tri-halophenoxyalkanoic acids and esters, amides and salts thereof.

Phenoxyalkanoic compounds of this type are described in a number of publications such as Ashton and Crafts, Mode of Action of Herbicides, 2nd Ed., Wiley and Sons, pp. 272-302 (1981).

According to this invention, the phenoxy acids can have the following general formula with varied substituent definitions:

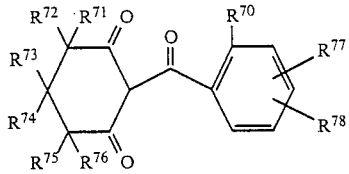

wherein x is an integer from 0 to 6, inclusive;

M, N and P are selected from the group consisting of hydrogen, halogen and lower alkyl having 1 to 4 carbon atoms, inclusive;

$R_1$ and $R_2$ are hydrogen or lower alkyl having 1 to 4 carbon atoms, inclusive;

X is oxygen or sulfur; and $R_3$ is selected from the group -$XR_4$,

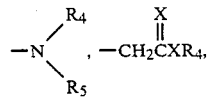

hydrogen, alkyl having from 1 to 6 carbon atoms, inclusive, aryl, aralkyl, alkoxyalkyl, alkylthioalkyl, alkylaminoalkyl, aryloxylakyl;

$R_4$ and $R_5$ are independnetly selected from the group consisting of hydrogen, alkyl having 1 to 6 carbon atoms, inclusive, aryl, aralkyl, alkoxyalkyl, alkylthioalkyl, alkylaminoalkyl, aryloxyalkyl;

$R_3$, $R_4$ and $R_5$ are independently selected from the group consisting of haloalkyl, alkenyl, haloalkenyl, alkylaryl, aryloxyalkyl, heterocyclicalkyl, cycloalkyl, furfuryl, tetrahydrofurfuryl, hydroxy, and —NHOH;

$R_4$ and $R_5$ taken together with the nitrogen can form a heterocyclic ring having from 2 to 6 carbon atoms, inclusive, quinoline and isoquinoline.

Preferably, the alkanoic acid portion has from about 2 to about carbon atoms, inclusive. Examples of suitable phenoxyalkanoic acid, salt, amide and ester compounds include: (2,4-dichlorophenoxy)acetic acid (2,4-D); (2,4,5-trichlorophenoxy)acetic acid; 4-(2,4-dichlorophenoxy)butyric acid; 4-[(4-chloro-o-tolyl)oxy]butyric acid; 2-[(4-chloro-o-tolyl)oxy]propionic acid; 2-(2,4-trichlorophenoxy)propionic acid; 2-(2,4dichlorophenoxy)propionic acid; dimethylamine salt of 3,6-dichloro-o-anisico acid (Dicamba); dimethylamine salt of p-chloro-o-methylphenoxyacetic acid (MCPA); di-n-butylamine salt of (2,4-dichlorohenoxy)acetic acid; and triethanolamine salt of 4-amine-3,5,6-trichloropicolinic acid; but does not exclude, any other generically covered compounds of the type known as "phenoxys".

Other aryloxyalkanoic or auxin-type compounds, either natural or synthetic, which are phytohormones and which cause extension of growth of plant cells include, for example, indole acetic acid and derivatives thereof; 4-chloroindole-3-acetic acid; phenylacetic acid; 4-[indol-3-yl]butyric acid; alpha-naphthylacetic acid; 2-naphthyloxyacetic acid; and 1-naphthylacetaxide.

The antidote is applied in conjunction with the herbicide in a non-phytotoxic antidotally effective amount. By "non-phytotoxic" is meant an amount of the antidote which causes at most minor or no injury to the desired crop species. By "antidotally effective" is meant an antidote used in an amount which is effective as an antidote with the herbicide to decrease the extent of injury caused by the herbicide to the desired crop species. The preferred weight ratio of herbicide to antidote is from about 0.1:1 to about 30:1. Another preferred weight ratio range is from about 1:1 to about 20:1. An even more preferred weight ratio range is from about 2:1 to about 15:1.

The following examples are for illustrative purposes only and are not intended as necessarily representative of the overall testing performed and are not intended to limit the invention in any way. As one skilled in the art is aware, in herbicidal testing, a significant number of factors that are not readily controllable can affect the results of individual tests and render them non-reproducible. For example, the results may vary depending on environmental factors, such as amount of sunlight and water, soil type, pH of the soil, temperature, and humidity, among other factors. Also, the depth of planting, the application rate of the herbicide, the application rate of the antidote, and the ratio of the herbicide-to-antidote application, as well as the nature of crops being tested, can affect the results of the test. Results may vary from crop to crop and within the crop varieties.

BIOLOGICAL EXAMPLES

The ability of the aryloxyalkanoic acid derviatives to protect, safen, reverse or otherwise antidote the effect of acylated 1,3-dicarbonyl herbicides can be inferred from the following examples.

EXAMPLE

Test with herbicide and antidote in sugarcane.

ANTIDOTAL EFFECT FIELD DATA

Tests 1–4 are under field conditions.
Phenoxy acetic acid antidote: Dimethylamine salt of 2,4-dichlorophenoxy acetic acid—2,4-D tank-mixed Test 1: Ratoon Sugarcane
Variety: NA 5679
Volume Application: 400 l/ha
Method and Stage of sugarcane at application:
POES (post-emergence surface)
Replications: 3
Results: 8 days after treatment (DAT)

| Compounds | Rate kg ai/ha | % of Plants with bleaching | % of the plant bleached |
|---|---|---|---|
| 51A | 1.0 | 10 | 5 |
| 51A + 2,4-D | 1.0 + 2.6 | 10 | 3 |
| 8D | 0.5 | 43 | 18 |
| 8D + 2,4-D | 0.5 + 2.16 | 0 | 0 |
| 24D | 0.25 | 63 | 22 |
| 24D + 2,4-D | 0.25 + 2.16 | 0 | 0 |
| 24D | 0.5 | 70 | 30 |
| 24D + 2,4-D | 0.5 + 2.16 | 3 | 2 |
| 4D | 1.0 | 70 | 28 |
| 4D + 2,4-D | 1.0 + 2.16 | 3 | 2* |

*Only plants treated with 4D + 2,4-D showed further late bleaching.

Test 2: Ratoon Sugarcane
Variety: NA 5679
Volume Application: 350 l/ha
Method and Stage of sugarcane at application:
POES, Sugarcane 35 cm high
Replications: 3
Results: 8 DAT

| Compounds | Rate kg ai/ha | % of Plants with bleaching | % of the plant bleached |
|---|---|---|---|
| 51A | 1.0 | 0 | 0 |
| 51A + 2,4-D | 1.0 + 2.6 | 0 | 0 |
| 8D | 0.5 | 100 | 15 |
| 8D + 2,4-D | 0.5 + 2.16 | 0 | 0 |
| 24D | 0.25 | 100 | 23 |
| 24D + 2,4-D | 0.25 + 2.16 | 0 | 0 |
| 24D | 0.5 | 100 | 32 |
| 24D + 2,4-D | 0.5 + 2.16 | 0 | 0 |
| 4D | 1.0 | 100 | 20 |
| 4D + 2,4-D | 1.0 + 2.16 | 0 | 0 |

Test 3: Ratoon Sugarcane
Variety: NA 5679
Volume Application: 325 l/ha
Method and Stage of sugarcane at application:
POES, Sugarcane 26 cm high
Replications: 3
Results: 8 DAT

| Compounds | Rate kg ai/ha | % of Plants with bleaching | % of the plant bleached |
|---|---|---|---|
| 51A | 1.0 | 4 | 1 |
| 51A + 2,4-D | 1.0 + 1.5 | 2 | 1 |
| 51A + 2,4-D | 1.0 + 2.0 | 2 | 1 |
| 51A − 2,4-D | 1.0 + 2.5 | 2 | 1 |
| 8D | 0.75 | 45 | 55 |
| 8D + 2,4-D | 0.75 + 1.5 | 0 | 0 |
| 8D + 2,4-D | 0.75 + 2.0 | 2 | 1 |
| 8D + 2,4-D | 0.75 + 2.5 | 0 | 0 |
| 24D | 0.25 | 100 | 60 |
| 24D + 2,4-D | 0.25 + 1.5 | 0 | 0 |
| 24D + 2,4-D | 0.25 + 2.0 | 5 | 1 |
| 24D + 2,4-D | 0.25 + 2.5 | 2 | 1 |
| 24D | 0.5 | 100 | 85 |
| 24D + 2,4-D | 0.5 + 1.5 | 0 | 0 |
| 24D + 2,4-D | 0.5 + 2.0 | 0 | 0 |
| 24D + 2,4-D | 0.5 + 2.5 | 0 | 0 |
| 4D | 1.0 | 75 | 60 |
| 4D + 2,4-D | 1.0 + 1.5 | 38 | 35 |
| 4D + 2,4-D | 1.0 + 2.0 | 45 | 35 |
| 4D + 2,4-D | 1.0 + 2.5 | 13 | 25 |

Test 4: Newly Planted Sugarcane
Variety: NA 5679
Volume Application: 400 l/ha
Method and Stage of sugarcane at application:
POES, Sugarcane at 20-25 cm high
Replications: 3
Results: 9 DAT

| Compounds | Rate kg ai/ha | % of Plants with Bleaching or Chlorosis | of the Plant Bleached or Chlorotic |
|---|---|---|---|
| 51A | 1.0 | 100 Chl | 5 Chl |
| 51A + 2,4-D | 1.0 + 2.6 | 33 Chl | 2 Chl |
| 8D | 0.5 | 30 Chl | 20 Chl |
| 8D + 2,4-D | 0.5 + 2.16 | 0 | 0 Chl* |
| 24D | 0.25 | 100 Bl | 18 Chl |
| 24D + 2,4-D | 0.25 + 2.16 | 0 | 0 |
| 24D | 0.5 | 87 Bl | 20 Bl |
| 24D + 2,4-D | 0.5 + 2.16 | 0 | 5 Chl* |

Chl = Chlorosis
Bl = Bleaching
*Only slight chlorosis was seen.

Results of greenhouse test conditions for 2,4-D (amine) antidote activity on surgacane varieties CP-5122, RB-735275 and RB-725147 are as follows:

Varieties CP-5122, RB-735275 and RB-725147

Volume of Water: 400 liters/ha
Method and Stage of Application: POES, sugarcane varieties at 30 cm high
Evaluation: Bleaching at 1, 2 and 3 weeks after application Symptoms observed and recorded are bleaching of the young sugarcone plants in the test, results indicate that the 2,4-D (dimethylamine) is independent of the rate tested and gave total protection to sugarcane from POES application of Compounds 24D and 8D.

Date Rated: 1, 2 and 3 weeks after application.

TEST FOR CONTINUED ANNUAL WEED ACTIVITY

Annual Weed Activity: Weeds in the 2-3 leaf stage were sprayed POES tank-mixed. Percent activity was taken 30 days after treatment.

| Compounds | kg ai/ha | % of Control (XG) | 30 DAT (X BL) |
|---|---|---|---|
| 51A | 1.0 | 91 | 74 |
| 51A + 2,4-D | 1.0 + 2.6 | 91 | 86 |
| 8D | 0.5 | 100 | 75 |
| 8D + 2,4-D | 0.5 + 2.16 | 100 | 95 |
| 24D | 0.25 | 100 | 99 |
| 24D + 2,4-D | 0.25 + 2.16 | 100 | 95 |
| 24D | 0.5 | 100 | 95 |
| 24D + 2,4-D | 0.5 + 2.16 | 100 | 94 |
| 4D | 1.0 | 98 | 69 |
| 4D + 2,4-D | 1.0 + 2.16 | 98 | 72 |

(XG) = Average of grasses: *Digitaria horizontalis* and *Eleusine indica*
(XBL) = Average of broadleaves: *Amaranthus hybridus, Acanthospermum hispidum, Ipomoea spp.* and *Portulaca oleracea*

Results show continued weed control on various grasses and broadleaf weed species with a sugarcane antidotally effective amount of 2,4-D with the herbicides.

PERENNIAL WEED ACTIVITY

Activity on Purple Nutsedge (*Cyperus rotundus*)

New field tests on 24D/2,4-D were carried out to confirm the POES activity of 24D mixture plus the antidote 2,4-D on *Cyperus rotundus*.

An advanced purple nutsedge stage of growth was selected for this test: *Cyperus rotundus*, 10 cm high.

Results showed that 2,4-D helped 24D to control purple nutsedge. 24D at 0.75 + 2,4-D or 24D alone at 1.0 kg ai/ha gave excellent POES control of purple nutsedge.

| Treatments | kg ai/ha | CP-5122 1 | CP-5122 2 | CP-5122 3 | RB-73525 1 | RB-73525 2 | RB-73525 3 | RB-725147 1 | RB-725147 2 | RB-725147 3 |
|---|---|---|---|---|---|---|---|---|---|---|
| 24D | 0.25 | 15 | 05 | 00 | 15 | 40 | 20 | 15 | 40 | 20 |
|  | 0.50 | 20 | 60 | 50 | 20 | 80 | 70 | 20 | 80 | 40 |
|  | 1.00 | 25 | 80 | 75 | 25 | 80 | 85 | 25 | 90 | 80 |
| 24D + 2,4D | 0.25 + 1.5 | 0 | 0 | 0 | 0 | 0 | 0 | 0 | 0 | 0 |
|  | 0.25 + 2.0 | 0 | 0 | 0 | 0 | 0 | 0 | 0 | 0 | 0 |
|  | 0.25 + 2.5 | 0 | 0 | 0 | 0 | 0 | 0 | 0 | 0 | 0 |
|  | 0.50 + 1.5 | 0 | 0 | 0 | 0 | 0 | 0 | 0 | 0 | 0 |
|  | 0.50 + 2.0 | 0 | 0 | 0 | 0 | 0 | 0 | 0 | 0 | 0 |
|  | 0.50 + 2.5 | 0 | 0 | 0 | 0 | 0 | 0 | 0 | 0 | 0 |
|  | 1.00 + 1.5 | 0 | 0 | 0 | 0 | 0 | 0 | 0 | 0 | 0 |
|  | 1.00 + 2.0 | 0 | 0 | 0 | 0 | 0 | 0 | 0 | 0 | 0 |
|  | 1.00 + 2.5 | 0 | 0 | 0 | 0 | 0 | 0 | 0 | 0 | 0 |
| 4D | 1.00 | 25 | 80 | 75 | 25 | 90 | 90 | 15 | 80 | 85 |
| 4D + 2,4-D | 1.00 + 1.5 | 20 | 80 | 80 | 20 | 60 | 90 | 10 | 20 | 60 |
|  | 1.00 + 2.0 | 20 | 70 | 70 | 20 | 15 | 30 | 10 | 0 | 30 |
|  | 1.00 + 2.5 | 10 | 40 | 70 | 10 | 15 | 40 | 10 | 0 | 20 |
| 51A | 1.00 | 0 | 0 | 0 | 0 | 0 | 0 | 0 | 0 | 0 |
| 51A + 2,4-D | 1.00 + 1.5 | 0 | 0 | 0 | 0 | 0 | 0 | 0 | 0 | 0 |
|  | 1.00 + 2.0 | 0 | 0 | 0 | 0 | 0 | 0 | 0 | 0 | 0 |
|  | 1.00 + 2.5 | 0 | 0 | 0 | 0 | 0 | 0 | 0 | 0 | 0 |
| 8D | 0.75 | 25 | 40 | 0 | 25 | 40 | 15 | 15 | 40 | 20 |
| 8D + 2,4-D | 0.75 + 1.5 | 0 | 0 | 0 | 0 | 0 | 0 | 0 | 0 | 0 |
|  | 0.75 + 2.0 | 0 | 0 | 0 | 0 | 0 | 0 | 0 | 0 | 0 |
|  | 0.75 + 2.5 | 0 | 0 | 0 | 0 | 0 | 0 | 0 | 0 | 0 |
| 2,4-D | 1.5 | 10 | 0 | 0 | 10 | 0 | 0 | 10 | 0 | 0 |
|  | 2.0 | 0 | 0 | 0 | 0 | 0 | 0 | 10 | 0 | 0 |
|  | 2.5 | 0 | 0 | 0 | 0 | 0 | 0 | 10 | 0 | 0 |

| Treatments | kg ai/ha | % of Visual control 27 DAT | % of Visual control 41 DAT | % Degree of Purple Nutsedge Plant 41 DAT |
|---|---|---|---|---|
| check | 0.5 | 573* | 214* | 214* |
| 24D | 0.5 | 45 | 60 | 57 |
| 24D + 2,4-D | 0.5 + 2.0 | 85 | 96 | 89 |
| 24D + 2,4-D | 0.5 + 2.5 | 92 | 98 | 96 |
| 24D | 0.75 | 50 | 68 | 69 |
| 24D + 2,4-D | 0.75 + 2.0 | 83 | 96 | 93 |
| 24D + 2,4-D | 0.75 + 2.5 | 87 | 96 | 96 |
| 24D | 1.0 | 73 | 92 | 96 |
| 24D + 2,4-D | 1.0 + 2.0 | 90 | 97 | 91 |
| 24D + 2,4-D | 1.0 + 2.5 | 93 | 99 | 96 |

*Number of purple nutsedge plants/m$^2$.

Tests carried out later under greenhouse conditions confirmed that 2,4-D did not change the weed activity of 24D.

Formulations

A formulation is the incorporation of a formulant in a form which is directly usable on crops and weeds. As defined herein, a "formulant" is the material which is to be formulated. The formulant may be either an antidote compound alone or an herbicide and antidote composition. The purpose of the formulation is to apply the formulant to the locus of a crop where it is desired to establish herbicidal selectivity by a convenient method. The "locus" may include soil, seeds, crop, crop seeds, seedlings and vegetation.

The antidotes described herein can be formulated in a number of ways for suitable application: (a) the antidote can be formulated for application directly to the crop seed; (b) the antidote and herbicide may be formulated separately and applied separately or applied simultaneously in an appropriate weight ratio, e.g., as a tank mix, or (c) the antidote and herbicide may be formulated together in the proper weight ratio.

Useful formulations of the compounds of this invention can be prepared in conventional ways. They include dusts, granules, microcapsules, pellets, solutions, suspensions, emulsions, wettable powders, emulsifiable concentrates and the like. Many of these may be applied directly to the locus. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active herbicide and antidote ingredient(s) and at least one of (a) about 0.1% to 20% surfactant(s) and (b) about 1% to 99.9% solid or liquid inert diluent(s). More specifically, they can contain these ingredients in the following approximate proportions.

TABLE 2

| Active Herb. & Ant. Ingredients | | Weight Percent* | |
|---|---|---|---|
| Compositions | | Diluent(s) | Surfactant(s) |
| Wettable Powders | 20-90 | 0-74 | 1-10 |
| Oil Suspensions Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength | 90-99 | 0-10 | 0-2 |

TABLE 2-continued

| Active Herb. & Ant. Ingredients | | Weight Percent* | |
|---|---|---|---|
| Compositions | | Diluent(s) | Surfactant(s) |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Dusts are free-flowing powder compositions containing the formulant impregnated on a particulate carrier. The particle size of the carriers is usually in the approximate range of 30 to 50 microns. Examples of suitable carriers are talc, bentonite, diatomaceous earth, and pyrophyllite. The composition generally contains up to 50% of formulant. Anti-caking and anti-static agents may also be added. Dusts may be applied by spraying from boom sprayers, hand sprayers or airplanes.

Wettable powders are finely divided compositions comprising a particular carrier impregnated with the formulant and additionally containing one or more surface active agents. The surface active agent promotes rapid dispersion of the powder in an aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in Wade Van Valkenburg, *Pesticide Formulations* (Marcel Dekker, Inc., N.Y., 1973) at pages 79-84.

Granules comprise the formulant impregnated on a particulate inert carrier having a particle size of about 1 to 2 millimeters (mm) in diameter. The granules can be made by spraying a solution of the formulant in a volatile solvent onto the granular carrier. Examples of suitable carries for the preparation of granules include clay, verminculite sawdust, and granular carbon.

Microcapsules and other slow release formulations are advantageous as formulations to deliver and distribute the active ingredients. Microcapsules consist of fully enclosed droplets or granules containing the active materials in which the enclosing material is an inert porous membrane, arranged to allow escape of the enclosed materials to the surrounding medium at controlled rates over a specified period of time. Encapsulated droplets are typically about 1 to 50 microns in diameter. The enclosed liquid typically constitutes about 50 to 95% of the weight of the entire capsule, and may contain an amount of solvent in addition to the active materials. Encapsulated granules are characterized by porous membranes sealing the openings of the granule carrier pores, trapping the liquid containing the active components inside for controlled release. A typical granule size ranges from 1 millimeter to 1 centimeter in diameter. In agricultural usage, the granule size is generally about 1 to 2 millimeters in diameter. Granules formed by extrusion, agglomeration or prilling are useful in the present invention as well as materials in their naturally occurring form. Examples of such carriers are vermiculite, sintered clay granules, kaolin, attapulgite clay, sawdust and granular carbon. Useful encapsulating materials include natural and synthetic rubbers, cellulosic materials, styrene-butadiene copolymers, polyacrylonitriles, polyacrylates, polyesters, polyamides, polyureas, polyurethanes and starch xanthates.

Emulsifiable concentrates consist of an oil solution of the formulant plus an emulsifying agent. Prior to use, the concentrate is diluted with water to form a suspanded emulsion of oil droplets. The emulsifiers used are usually a mixture of anionic and nonionic surfactants. Other additives, such as suspending agents and thickeners, may be included in the emulsifiable concentrate.

When the formulant is an antidote and herbicide composition, the proportion of antidote compound to herbicide compound generally ranges from approximately 0.001 to 30 parts by weight of the antidote compound per weight of the herbicide compound.

Formulations generally contain several additives in addition to the formulant and carrier or agent. Among these are inert ingredients, diluent carriers, organic solvents, water, oil and water, water in oil emulsions, carriers of dusts and granules, and surface active wetting, dispersing and emulsifying agents. Fertilizers, e.g., ammonium nitrate urea and superphosphate, may be included. Aids to rooting and growth, e.g., compost, manure, humus and sand, may also be included.

Alternatively, the antidote compounds and herbicide and antidote compositions of this invention can be applied to a crop by addition of the formulant to irrigation water supplied to the field to be treated. This method of application permits the penetration of the compositions into the soil as the water is absorbed.

As another alternative, the formulant can be applied to the soil in the form of a solution in a suitable solvent. Solvents frequently used in these formulations include kerosene, fuel oil, xylene, petroleum fractions with boiling ranges above xylene and aromatic petroleum fractions rich in methylated naphthalenes. Liquid solutions, like dusts, may be applied by spraying from boom and hand sprayers or airplanes.

EXAMPLE

Dusts: The following substances are used to formulate (a) 5% and (b) a 2% dust:

(a)
5 parts of active substance
95 parts of talc;
(b)
2 parts of active substance
1 part of highly dispersed silicic acid
97 parts of talc.

The active substances are mixed with the carriers and ground and in this form can be processed to dusts for application.

EXAMPLE

Granulate: The following substances are used to formulate a 5% granulate:

5 parts of active substance
0.25 part of epichlorohydrin
0.25 part of cetyl polyglycol ether -continued 3.25 parts of polyethylene glycol
91 parts of kaolin (particle size 0.3-0.8 mm).

The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo.

EXAMPLE

Wettable powders: The following constituents are used to formula (a) a 70%, (b) a 40%, (c) and (d) a 25% and (e) a 10% wettable powder.

(a)
70 parts of active substance
5 parts of sodium dibutylnaphthylsulfonate
3 parts of naphthalenesulfonic acid/phenolsulfonic acid/formaldehyde condensate (3:2:1)
10 parts of kaolin
12 parts of Champagne chalk
(b)
40 parts of active substance
5 parts of sodium ligninsulfonate
1 part of sodium dibutylnaphthalenesulfonic acid
54 parts of silicic acid
(c)
25 parts of active substance
4.5 parts of calcium ligninsulfate
1.9 parts of Champagne chalk/hydroxyethyl cellulose mixture (1:1)
1.5 parts of sodium dibutylnaphthalenesulfonate
19.5 parts of silicic acid
19.5 parts of Champagne chalk
28.1 parts of kaolin
(d)
25 parts of active substance
2.5 parts of isooctylphenoxy-polyethylene-ethanol
1.7 parts of a Champagne chalk/hydroxyethyl cellulose mixture (1:1)
8.3 parts of sodium aluminum silicate
16.5 parts of kieselguhr
46 parts of kaolin
(e)
10 parts of active substance
3 parts of a mixture of the sodium salts of saturated fatty alcohol sulfates
5 parts of naphthalenesulfonic acid/formaldehyde condensate
82 parts of kaolin.

The active substances are intimately mixed in suitable mixers with the additives and ground in appropriate mills and rollers. Wettable powders of excellent wettability and suspension power are obtained. These wettable powders can be diluted with water to give suspensions of the desired concentration and can be used in particular for treating parts of plants.

EXAMPLE

Emulsifiable concentrate: The following substances are used to formulate a 25% emulsifiable concentrate:

25 parts of active substance
2.5 parts of epoxidized vegetable oil
10 parts of an alkylarylsulfonate/fatty alcohol polyglycol ether mixture
5 parts of diethylformamide
57.5 parts of xylene.

By diluting such a concentrate with water it is possible to prepare emulsions of the desired concentrations, which are especially suitable for leaf application.

What is claimed is:

1. The herbicide composition comprising as the herbicidally active ingredient, an herbicidally effective amount of an acylated 1,3-dicarbonyl compound having the formula

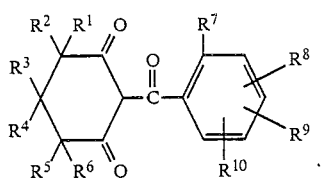 (II)

in which $R^1$, $R^2$, $R^3$, $R^4$, $R^5$ and $R^6$ are independently hydrogen or $C_1$-$C_4$ alkyl or $R^1$ or $R^3$ is

in which $R_a$ is $C_1$-$C_4$ alkyl; phenyl, optionally substituted by from 2 to 5 methyl groups;

or in which $R^1$ and $R^2$, or $R^3$ and $R^4$, taken together are $C_2$-$C_5$ alkylene (such compounds have a spiro structure);

$R^7$ is halogen (chlorine, bromine, iodine or fluorine); cyano; $C_1$-$C_4$ alkyl; $C_1$-$C_4$ haloalkyl; $R_kSO_n$ in which $R_k$ is $C_1$-$C_4$ alkyl and n=0, 1 or 2; $C_1$-$C_4$ alkoxy; or nitro;

$R^8$, $R^9$ and $R^{10}$ independently are hydrogen or substituents including halogen; $C_1$-$C_4$ alkyl; $C_1$-$C_4$ alkoxy; trifluoromethoxy; cyano; nitro; $C_1$-$C_4$ haloalkyl; $C_1$-$C_4$ alkylthio; phenoxy; or substituted phenoxy in which the substituent is halogen or halomethyl or both;

$R_bS(O)_n$ in which n is 0, 1 or 2; and $R_b$ is $C_1$-$C_4$ alkyl, $C_1$-$C_4$ haloalkyl, phenyl or benzyl, $$R_cCNH-$$
$$\overset{O}{\underset{\|}{}}$$

in which $R_c$ is $C_1$-$C_4$ alkyl,

—$NR_dR_e$ in which $R_d$ and $R_e$ independently are hydrogen or $C_1$-$C_4$ alkyl;

$R_fC(O)$— in which $R_f$ is hydrogen, $C_1$-$C_4$ alkyl, $C_1$-$C_4$ haloalkyl or $C_1$-$C_4$ alkoxy;

$SO_2NR_gR_h$ in which $R_g$ and $R_h$ independently are hydrogen or $C_1$-$C_4$ alkyl;

and as an antidote compound therefor, a nonphytotoxic antidotally effective amount of 2,4-dichlorophenoxyacetic acid or salt, amide or ester thereof wherein said phenoxyacetic acid compound is antidotally active with said herbicide and wherein the weight ratio of herbicide to antidote compound is from about 0.1:1 to about 30:1.

2. A herbicide composition comprising as the herbicidally active ingredient a compound of the formula

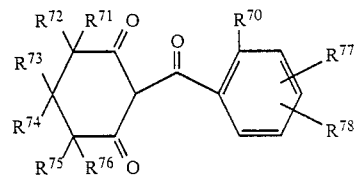

wherein $R^{70}$ is halogen; $C_1$-$C_2$ alkyl; $C_1$-$C_2$ alkoxy; trifluoromethoxy; difluoromethoxy; nitro; cyano; $C_1$-$C_2$ haloalkyl; $R^aSO_n$— wherein n is 0 or 2; and $R^a$ is $C_1$-$C_2$ alkyl; trifluoromethyl or difluoromethyl; cyano, nitro $C_1$-$C_2$ alkylthio or $C_1$-$C_2$ alkylsulfonyl; and $R^{71}$ is hydrogen; $C_1$-$C_4$ alkyl; halogen; phenyl; or substituted phenyl;

$R^{72}$ is hydrogen or $C_1$-$C_4$ alkyl; or $R^{71}$ and $R^{72}$ together are $C_2$-$C_5$ alkylene;

$R^{73}$ is hydrogen; $C_1$-$C_4$ alkyl; phenyl; or substituted phenyl, with the proviso that $R^{71}$ and $R^{73}$ are not both phenyl or substituted phenyl;

$R^{74}$ is hydrogen or $C_1$-$C_4$ alkyl;

$R^{75}$ is hydrogen, halogen or $C_1$-$C_4$ alkyl;

$R^{76}$ is halogen, nitro, cyano, trifluoromethyl; —C(O)$NR_2^b$ wherein $R^b$ is hydrogen or $C_1$-$C_2$ alkyl; and $R^{77}$ and $R^{78}$ independently are (1) hydrogen; (2) halogen; (3) $C_1$-$C_4$ alkyl; (4) $C_1$-$C_4$ alkoxy; (5) trifluoromethoxy; (6) cyano; (7) nitro; (8) $C_1$-$C_4$ haloalkyl; (9) $R^bSO_n$— wherein n is the integer 0, 1 or 2; and $R^b$ is (a) $C_1$-$C_4$ alkyl;

(b) $C_1$-$C_4$ alkyl substituted with halogen or cyano;

(c) phenyl; or (d) benzyl;

(10) —$NR^cR^d$; —$SO_2NR^{cd}$, and —$N(R^c)C(O)R^d$ wherein $R^c$ and $R^d$ independently are hydrogen or $C_1$-$C_4$ alkyl; or

(11) $R^eC(O)$—wherein $R^e$ is $C_1$-$C_4$ alkyl or $C_1$-$C_4$ alkoxy; and as an antidote compound therefor, a nonphytotoxic antidotally effective amount of 2,4-dichlorophenoxyacetic acid or salt, amide or ester thereof wherein said phenoxyacetic acid compound is antidotally active with said herbicide and wherein the weight ratio of herbicide to antidote compound is from about 0.1:1 to about 30:1.

3. The method of reducing injury to sugarcane caused by an acylated 1,3-dicarbonyl containing herbicidal compound having the formula

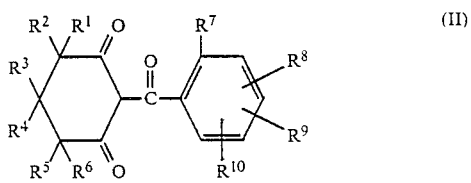

in which $R^1$, $R^2$, $R^3$, $R^4$, $R^5$ and $R^6$ are independently hydrogen or $C_1$-$C_4$ alkyl or $R^1$ or $R^3$ is

in which

R$_a$ is C$_1$–C$_4$ alkyl; phenyl, optionally substituted by from 2 to 5 methyl groups;

or in which R$^1$ and R$^2$, or R$^3$ and R$^4$, taken together are C$_2$–C$_5$ alkylene (such compounds have a spiro structure);

R$^7$ is halogen (chlorine, bromine, iodine or fluorine); cyano; C$_1$–C$_4$ alkyl; C$_1$–C$_4$ haloalkyl; R$_k$SO$_n$ in which R$_k$ is C$_1$–C$_4$ alkyl and n=0, 1 or 2; C$_1$–C$_4$ alkoxy; or nitro;

R$^8$, R$^9$ and R$^{10}$ independently are hydrogen or substituents including halogen; C$_1$–C$_4$ alkyl; C$_1$–C$_4$ alkoxy, trifluoromethoxy; cyano; nitro; C$_1$–C$_4$ haloalkyl; C$_1$–C$_4$ alkylthio; phenoxy; or substituted phenoxy in which the substituent is halogen or halomethyl or both;

R$_b$S(O)$_n$ in which n is 0, 1 or 2; and R$_b$ is C$_1$–C$_4$ alkyl, C$_1$–C$_4$ haloalkyl, phenyl or benzyl,

in which R$_c$ is C$_1$–C$_4$ alkyl,

—NR$_d$R$_e$ in which R$_d$ and R$_e$ independently are hydrogen or C$_1$–C$_4$ alkyl;

R$_f$C(O)— in which R$_f$ is hydrogen, C$_1$–C$_4$ alkyl, C$_1$–C$_4$ haloalkyl or C$_1$–C$_4$ alkoxy;

SO$_2$NR$_g$R$_h$ in which R$_g$ and R$_h$ independently are hydrogen or C$_1$–C$_4$ alkyl; and which comprises applying to the soil, crop or crop seed as an antidote compound therefor, a nonphytotoxic antidotally effective amount of 2,4-dichlorphenoxyacetic acid or salt, amide or ester thereof wherein said phenoxyacetic acid compound is antidotally active with said herbicide and wherein the weight ratio of herbicide to antidote compound is from about 0.1:1 to about 30:1.

4. The method of reducing injury to sugarcane caused by an acylated 1,3-dicarbonyl containing herbicide compound having the formula

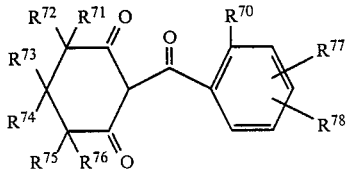

wherein

R$^{70}$ is halogen; C$_1$–C$_2$ alkyl; C$_1$–C$_2$ alkoxy; trifluoromethyl; difluoromethoxy; nitro; cyano; C$_1$–C$_2$ haloalkyl; R$^a$SO$_n$— wherein n is 0 or 2; and R$^a$ is C$_1$–C$_2$ alkyl; trifluoromethyl or difluoromethyl; cyano, nitro C$_1$–C$_2$ alkylthio or C$_1$–C$_2$ alkylsulfonyl; and R$^{71}$ is hydrogen; C$_1$–C$_4$ alkyl; halogen; phenyl; or substituted phenyl;

R$^{72}$ is hydrogen or C$_1$–C$_4$ alkyl; or

R$^{71}$ and R$^{72}$ together are C$_2$–C$_5$ alkylene;

R$^{73}$ is hydrogen; C$_1$–C$_4$ alkyl; phenyl; or substituted phenyl, with the proviso that R$^{71}$ and R$^{73}$ are not both phenyl or substituted phenyl;

R$^{74}$ is hydrogen or C$_1$–C$_4$ alkyl;

R$^{75}$ is hydrogen, halogen or C$_1$–C$_4$ alkyl;

R$^{76}$ is halogen, nitro, cyano, trifluoromethyl; —C(O)NR$_2^b$ wherein R$^b$ is hydrogen or C$_1$–C$_2$ alkyl; and R$^{77}$ and R$^{78}$ independently are (1) hydrogen; (2) halogen; (3) C$_1$–C$_4$ alkyl; (4) C$_1$–C$_4$ alkoxy; (5) trifluoromethoxy; (6) cyano; (7) nitro; (8) C$_1$–C$_4$ haloalkyl; (9) R$^b$SO$_n$— wherein n is the integer 0, 1 or 2; and R$^b$ is (a) C$_1$–C$_4$ alkyl;
 (b) C$_1$–C$_4$ alkyl substituted with halogen or cyano;
 (c) phenyl; or
 (d) benzyl;

(10) —NR$^c$R$^d$; —SO$_2$NR$^{cd}$, and —N(R$^c$)C(O)R$^d$ wherein

R$^c$ and R$^d$ independently are hydrogen or C$_1$–C$_4$ alkyl; or (11) R$^e$C(O)— wherein R$^e$ is C$_1$–C$_4$ alkyl or C$_1$–C$_4$ alkoxy;

which comprises applying to the soil, crop or crop seed as an antidote compound therefor, a nonphytotoxic antidotally effective amount of 2,4-dichlorophenoxyacetic acid or salt, amide or ester thereof wherein said phenoxyacetic acid compound is antidotally active with said herbicide and wherein the weight ratio of herbicide to antidote compound is from about 0.1:1 to about 30:1.

5. A composition for protecting sugarcane from the phytotoxic effect of acylated 1,3-dicarbonyl herbicides as defined in claim 1 or 2, which composition contains as a safener component a nonphytotoxic antidotally effective amount of a 2,4-dichlorophenoxy acetic acid, salt, amide or ester thereof together with an inert carrier.

6. A method for protecting sugarcane from the phytotoxic effect of acylated 1,3-dicarbonyl herbicides as defined in claim 1 or 2, which comprises applying as a postemergence treatment a composition containing as an antidote component a nonphytotoxic antidotally effective amount of 2,4-dichlorophenoxyacetic acid, salt, amide or ester thereof, together in an inert carrier.

* * * * *